(12) United States Patent
Webster et al.

(10) Patent No.: US 11,273,067 B2
(45) Date of Patent: Mar. 15, 2022

(54) ORTHOPEDIC DEVICE FOR SCAPULOTHORACIC STABILIZATION

(71) Applicant: Ossur Iceland ehf, Reykjavik (IS)

(72) Inventors: Christopher C. Webster, Foothill Ranch, CA (US); Orr Limpisvasti, Foothill Ranch, CA (US); Harry Duane Romo, Foothill Ranch, CA (US); Jared Olivo, Foothill Ranch, CA (US); Zachariah J. Klutts, Foothill Ranch, CA (US); Lindsay Frost, Foothill Ranch, CA (US); Mark Harman Powell, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 380 days.

(21) Appl. No.: 16/531,861

(22) Filed: Aug. 5, 2019

(65) Prior Publication Data
US 2019/0350738 A1    Nov. 21, 2019

Related U.S. Application Data

(63) Continuation of application No. 15/082,518, filed on Mar. 28, 2016, now Pat. No. 10,376,404.
(Continued)

(51) Int. Cl.
*A61F 5/01*    (2006.01)
*A61F 5/02*    (2006.01)
(Continued)

(52) U.S. Cl.
CPC ............ *A61F 5/026* (2013.01); *A61F 5/0118* (2013.01); *A61F 5/02* (2013.01); *A61F 5/028* (2013.01);
(Continued)

(58) Field of Classification Search
CPC .......... A61F 5/026; A61F 5/3723; A61F 5/37; A61F 5/03; A61F 5/028; A61F 5/02;
(Continued)

(56) References Cited

U.S. PATENT DOCUMENTS 472,086 A    4/1892  Town
559,024 A    4/1896  Bessing
(Continued)

FOREIGN PATENT DOCUMENTS

DE    1147711 B    4/1963
EP    0781536 A1   7/1997
(Continued)

OTHER PUBLICATIONS

"Shoulder Stabilizer and Shoulder Stabilizer S.P.A." Sawathotics, Donjoy, www.donjoy.com, 2006 dj Orthopedics, LLC.
(Continued)

*Primary Examiner* — Tarla R Patel
(74) *Attorney, Agent, or Firm* — Workman Nydegger

(57) ABSTRACT

An orthopedic device is arranged for scapulothoracic stabilization, inclusive of features for biomechanical stabilization of the shoulder, scapula and spine, treated alone or in combination with assembly features for supporting an arm or shoulder. The orthopedic device may be arranged in a garment or shoulder harness such that either may include first and second strap systems for extending over first and second shoulders of a user, respectively, and each of the first and second strap systems forms a "Figure 9" shape about the respective shoulder, with a strap section arranged to extend toward a waist stabilizer that may form part of the orthopedic device.

17 Claims, 12 Drawing Sheets

Related U.S. Application Data

(60) Provisional application No. 62/241,900, filed on Oct. 15, 2015, provisional application No. 62/139,181, filed on Mar. 27, 2015.

(51) Int. Cl.
　　*A61F 5/03*　　(2006.01)
　　*A61F 5/37*　　(2006.01)
　　*A61F 5/058*　　(2006.01)

(52) U.S. Cl.
　　CPC ............ *A61F 5/03* (2013.01); *A61F 5/05858* (2013.01); *A61F 5/37* (2013.01); *A61F 5/3723* (2013.01); *A61F 5/3746* (2013.01); *A61F 5/3753* (2013.01)

(58) Field of Classification Search
　　CPC .. A61F 5/3753; A61F 5/3746; A61F 5/05858; A61F 5/0118
　　See application file for complete search history.

(56) References Cited

U.S. PATENT DOCUMENTS

| | | | |
|---|---|---|---|
| 1,257,297 | A | 2/1918 | Brown |
| 2,310,566 | A | 2/1943 | Anderson |
| 2,661,000 | A | 12/1953 | Gazeley et al. |
| 3,116,735 | A | 1/1964 | Geimer |
| 3,906,944 | A | 9/1975 | Christen |
| 4,254,950 | A | 3/1981 | Baumann |
| 4,785,803 | A | 11/1988 | Benckhuijsen |
| 5,466,214 | A | 11/1995 | Calderon-Garciduenas |
| 5,487,724 | A | 1/1996 | Schwenn |
| 5,582,583 | A | 12/1996 | Ballantyne |
| 5,606,745 | A | 3/1997 | Gray |
| 5,658,241 | A | 8/1997 | Deharde et al. |
| 5,683,353 | A | 11/1997 | Hamersly |
| 5,839,122 | A | 11/1998 | Dicker et al. |
| 5,857,990 | A | 1/1999 | Maas |
| 5,937,442 | A | 8/1999 | Yamaguchi et al. |
| 5,954,621 | A | 9/1999 | Joutras et al. |
| 6,231,488 | B1 | 5/2001 | Dicker et al. |
| 6,398,746 | B2 | 6/2002 | Bramlage et al. |
| 7,081,101 | B1 | 7/2006 | Sawa |
| 7,516,498 | B2 | 4/2009 | Torry |
| 7,861,319 | B2 | 1/2011 | Torry |
| 7,871,388 | B2* | 1/2011 | Brown .................... A61F 5/026 602/19 |
| 7,955,285 | B2 | 6/2011 | Bonutti et al. |
| 8,047,893 | B2 | 11/2011 | Fenske |
| 8,172,779 | B2 | 5/2012 | Ingimundarson et al. |
| 8,296,864 | B2 | 10/2012 | Torry |
| 8,533,864 | B1 | 9/2013 | Kostrzewski |
| 8,808,212 | B1 | 8/2014 | Redmond |
| 8,905,956 | B2 | 12/2014 | Waeger |
| 9,125,442 | B2* | 9/2015 | Brown .................... A61F 5/026 |
| 9,220,625 | B2* | 12/2015 | Ingimundarson ....... A61F 5/024 |
| 9,370,440 | B2* | 6/2016 | Ingimundarson ....... A61F 5/026 |
| 9,572,705 | B2* | 2/2017 | Ingimundarson ....... A61F 5/026 |
| 2003/0149386 | A1 | 8/2003 | Ceriani et al. |
| 2007/0270976 | A1 | 11/2007 | Deharde et al. |
| 2008/0249438 | A1 | 10/2008 | Agrawal et al. |
| 2010/0144492 | A1 | 6/2010 | Ruan |
| 2011/0021962 | A1 | 1/2011 | Sorrenti |
| 2011/0131697 | A1 | 6/2011 | Kawahara |
| 2011/0251539 | A1 | 10/2011 | Gentz et al. |
| 2012/0059297 | A1* | 3/2012 | Newkirk ................. A61F 5/026 602/19 |
| 2012/0059298 | A1 | 3/2012 | Hoffman et al. |
| 2012/0101420 | A1 | 4/2012 | Albrecht et al. |
| 2012/0150085 | A1 | 6/2012 | Kayser |
| 2012/0316483 | A1* | 12/2012 | Waeger .................... A61F 5/026 602/19 |
| 2013/0090585 | A1 | 4/2013 | Bue, Jr. et al. |
| 2013/0104280 | A1 | 5/2013 | Boynton |
| 2013/0190670 | A1 | 7/2013 | Von Zieglauer |
| 2013/0296756 | A1 | 11/2013 | Troncoso |
| 2014/0081189 | A1 | 3/2014 | Ingimundarson et al. |
| 2014/0336555 | A1 | 11/2014 | Barbosa |
| 2015/0040286 | A1 | 2/2015 | Schultz et al. |
| 2015/0094634 | A1 | 4/2015 | Waeger |

FOREIGN PATENT DOCUMENTS

| | | |
|---|---|---|
| JP | 2013087385 A | 5/2013 |
| JP | 2014030675 A | 2/2014 |
| WO | 2009093180 A1 | 7/2009 |
| WO | 2012014164 A2 | 2/2012 |
| WO | 2012168883 A1 | 12/2012 |
| WO | 2013116900 A1 | 8/2013 |
| WO | 2013138468 A1 | 9/2013 |

OTHER PUBLICATIONS

"Bracing and Supports Catalog" Ottobock, www.ottobockOrthopedicservices.com, 2015 Otto Bock Healthcare LP.
"Product Catalog Supports and Orthoses, Motion is Life" Bauerfeind, www.bauerfeind.com, Retrieved Mar. 2016.
Brochure, "Quadrant Shoulder Brace" Donjoy, dj Orthopedics LLC, Retrieved Mar. 2016.
Brochure, "Soe Unique Arc 2.0" Bledsoe, www.bledsoebrace.com, 2011 Medical technology inc., dba Bledsoe Brace Systems.
International Search Report from corresponding PCT Application No. PCT/US2016/024439, dated Aug. 10, 2016.

* cited by examiner

ORTHOPEDIC DEVICE FOR SCAPULOTHORACIC STABILIZATION

FIELD OF THE DISCLOSURE

The disclosure relates to an orthopedic device for scapulothoracic stabilization, inclusive of features for biomechanical stabilization of the shoulder, scapula and spine, treated alone or in combination with assembly features for supporting an arm or shoulder.

BACKGROUND

Certain pathological conditions may benefit from scapulothoracic stabilization. Optimal posture includes not only cervical, thoracic and spinal alignment in coronal and saggital planes, but it also includes appropriate scapulothoracic and concomitant sternal clavicular and acromial clavical alignment.

Traditional thoracic lumbar sacral orthosis (TLSO) braces or supports, and often referred to as dorsolumbar corsets, have existed for many years. Early designs focused on including a non-stretch cotton ducking, with a hook and eye closure on the anterior side of the support. Laces are along the sides of the support to allow for circumferential reduction. Tightening of the laces creates abdominal compression with the intention of raising intracavitary pressure that should internally reduce a load on a vertebral column.

Channels are sewn onto the fabric to form pockets allowing for rigid stays to be added at locations of the support. Stays located over the abdominal region create extra stabilization of the abdominal tissue of a user. Long paraspinal stays are located over the paraspinal musculature extending from the sacrum to the level of the spine of the scapula to enhance saggital plane stabilization of the thoracic-lumbar-sacral spine. Axillary straps are used to attach proximally at the posterior proximal aspect of the support to course over the shoulder and draw down through the axilla.

The combination of materials used in the support, areas of compression, and the stays and the axillary straps function together to provide moderate stabilization of the thoracic-lumbar-sacral spine in the sagittal plane while improving shoulder posture.

While effective, the known supports are heavy, cumbersome and deter users from wearing them. Due to their size, they inhibit mobility and appear unwieldy which limits their desirability by users.

SUMMARY

The disclosure relates to an orthopedic device for scapulothoracic stabilization, inclusive of features for biomechanical stabilization of the shoulder, scapula and spine, treated alone or in combination with shoulder support such as a shoulder brace assembly or shoulder sling. The orthopedic device may be provided as a stabilization garment or a shoulder harness in combination with the stabilization garment or provided alone, both relying on similar structure for stabilizing the shoulders and distributing pressure. The stabilization garment and shoulder harness may be provided in combination with an assembly feature such as a shoulder sling, brace assembly or other suitable assembly feature or combination thereof.

In a simplified embodiment, the orthopedic device has anterior and posterior sides, and is adapted for securing over first and second opposed shoulders on first and second lateral sides of a user, respectively. The orthopedic device comprises a waist stabilizer adapted to secure about a waist. A first strap system extends over a first shoulder of a user on the first lateral side. The first strap system has a first strap section generally forming a loop over the anterior and posterior sides, and a second strap section extending obliquely and downwardly from the first strap section in a first direction toward the waist stabilizer thereby forming a "Figure 9" shape. A second strap system extends over a second shoulder of a user on the second lateral side. The second strap system has a first strap section generally forming a loop over the anterior and posterior sides, and a second strap section extending obliquely and downwardly in a second direction toward the waist.

A first direction of the second strap section of the first strap system may extend in a generally opposed angle relative to the second direction by which the second strap section of the second strap system extends. The second strap sections of the first and second strap systems preferably cross one another over a posterior side of the orthopedic device. The second strap section of the first strap system is arranged to secure to the waist stabilizer by mutually cooperating fasteners.

The second strap system may secure to a lateral support located proximate or adjacent the waist stabilizer on the first lateral side, or to the waist stabilizer. The second strap system preferably includes a third strap section extending from the anterior side of the first strap section and the second strap section extends from the posterior side of the first strap section, the second and third strap sections connecting to the waist stabilizer. In at least one variation, the second and third strap sections connect to the waist stabilizer by a lateral support secured to the waist stabilizer on the first lateral side. A shoulder support secures to the lateral support on the first lateral side.

Either or both of the first and second strap systems forms a Y-shape about the posterior side of the orthopedic device with portions of the first strap section forming the loop on the posterior side joining the second strap section at a junction. The junction enables adjustability of a length of the first strap section, and a length of the second strap section of the first strap system. The first and second strap sections of the first strap system are discontinuous and secured to one another only via the junction.

According to embodiments of the body stabilization garment, different textile materials are used to form panels in a garment, which are lightweight, breathable, thin, unobtrusive and have different elastic properties. Lightweight and breathable frictional padding materials are employed to provide combined properties of friction and compressibility to enhance the properties of the textile-based panels. Uniquely placed, structured and functioning straps are included to yet further enhance the textile materials and frictional padding materials to enable corrective action to a user without unobtrusive structural features and inhibiting migration of the vest over the user's body. The features of the body stabilization garment improve stabilization of the shoulder, scapula and spine while offering a user with increased comfort and leads to increased user compliance.

Indications of the garment, as with the shoulder harness, include compression fracture, osteoporosis, hyperkyphosis and thoracic outlet syndrome, post-operative motion restriction, and spondylolisthesis. Also, the garment or shoulder harness, or generally the orthopedic device, may be used for non-surgical or post-op shoulder conditions, and post injury rehabilitation requiring a user's arm to be positioned in a fixed configuration In the embodiments, truncal foundational support is provided by a waist stabilizer arranged to offer abdominal compression. The garment may be used in combination with removable, thermoformable and trimmable anterior and posterior plates securable to exterior or interior portions of the garment, and in combination with the waist stabilizer. The waist stabilizer may serve as a foundation for the garment including movement, restraint and retention on the user, and offer desirable compression for the user at the lumbar region.

The garment includes first and second shoulder straps having a "Figure 9" configuration adapted about the axilla to provide biomechanically relevant acromio-clavicular stabilization and positioning for improved posture such as scapular retraction and depression. The shoulder straps have first and second anchor portions secured to an anterior side of the garment and extend about the shoulder to a junction on the posterior side of the garment at which they form a "Y" junction with a third anchor portion adapted to removably secure to the anterior side of the garment. The shoulder strap configuration for each shoulder enables clavicular and serratus anterior regions of the garment and simultaneously controls scapular retraction and depression.

The garment has localized areas of non-stretch or inelastic panels for creating biomechanically effective control zones by textile stabilization, with elastic or semi-elastic panels for enabling greater user movement. Even among the panels, which may be formed from a textile, different gradations of elasticity may be provided depending on the surface area and material composition of the panels. The panels, depending on their elasticity or inelasticity, surface area and location, create biomechanical guidance of movement and freedom of motion for the user.

Frictional sections are in localized areas, preferably along the interior side of the garment, enabling secure capture of dermal layers of the user for concomitant bony structures. The frictional sections may correspond to elastic or inelastic sections of the garment, and the frictional sections may be elastic, inelastic or semi-elastic. The frictional sections may have a thickness or be arranged with padding formed by a compressible material having compressibility greater than the panels.

The aforementioned features and benefits of the embodiments of the garment provide a lightweight and comfortable garment encouraging frequent and daily use by a user. The localized panels and their strategic locations, whether considered alone or in combination with the shoulder straps and waist stabilizer, offer biofeedback to promote functional healing. The breathability of the panels in combination with the breathable frictional sections enables moisture control for comfort during all day use with antimicrobial inhibition for odor control, particularly both the panels and the frictional sections. The thin and streamlined nature of the panels and frictional sections allow for the user to wear the garment under personal clothing without being obtrusive.

Similar to the garment, shoulder harness embodiments rely on the "Figure 9" system on the contra shoulder (relative to the injury) to suspend a shoulder support such as a sling or brace assembly. The shoulder harness likewise employs a generally Y-shape formation of at least a strap system extending from the contra shoulder. The shoulder harness enables scapular stabilization on the ipsilateral side (affected shoulder or side) with the strap system to create scapular stabilization of the glenohumeral joint, preferably on the truncal side, and stabilizes the humeral side of the glenohumeral joint.

The foregoing is provided as information, which may be useful for better understanding this disclosure. Other aspects and features of illustrative embodiments will become apparent to those ordinarily skilled in the art upon review of the following description of such embodiments in conjunction with the accompanying figures.

BRIEF DESCRIPTION OF THE DRAWINGS

These and other features, aspects, and advantages of the present disclosure will become better understood regarding the following description, appended claims, and accompanying drawings.

Figure 1:
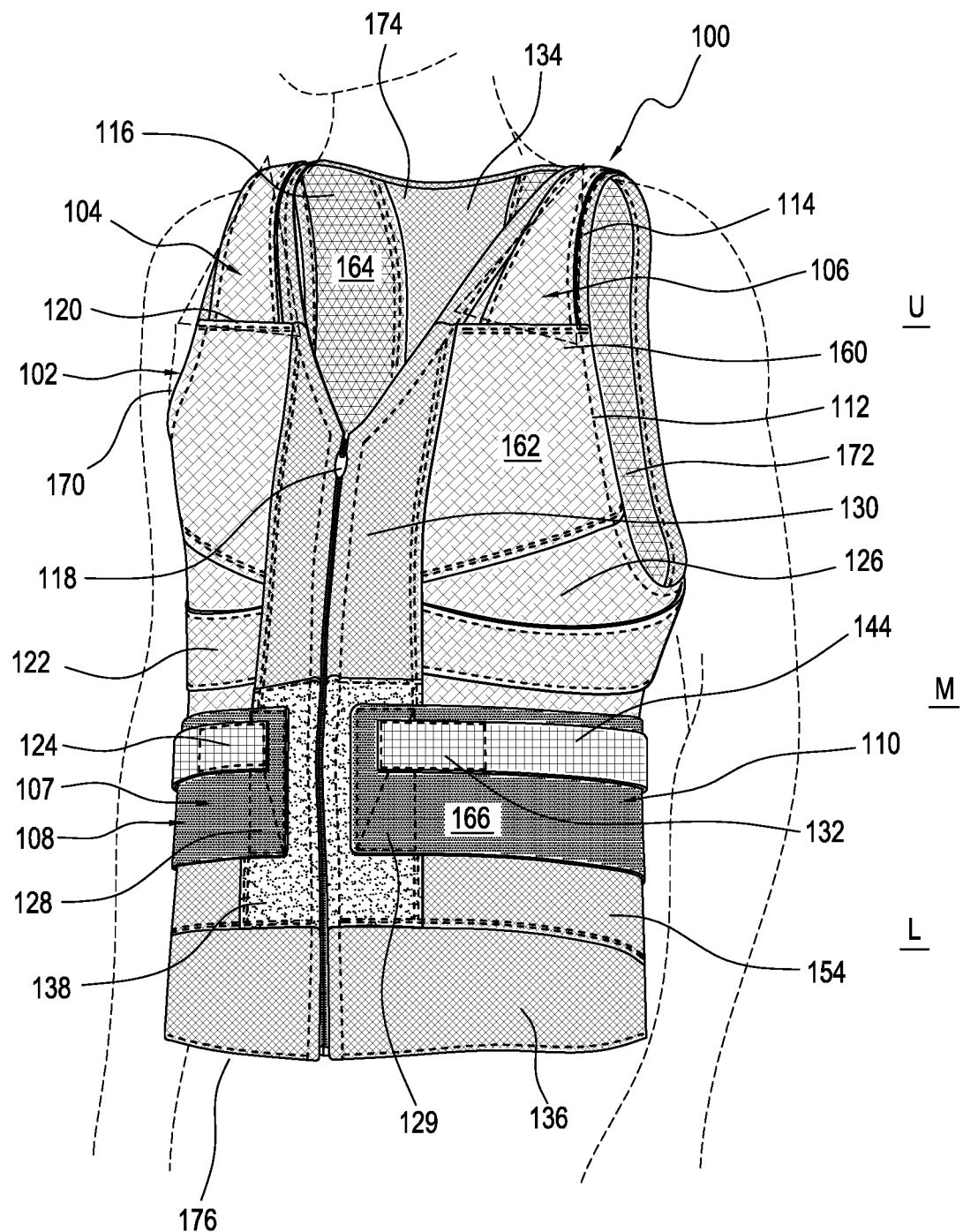
FIG. 1 is an anterior perspective view of an orthopedic device for scapulothoracic stabilization in the form of a garment.
Figure 2:
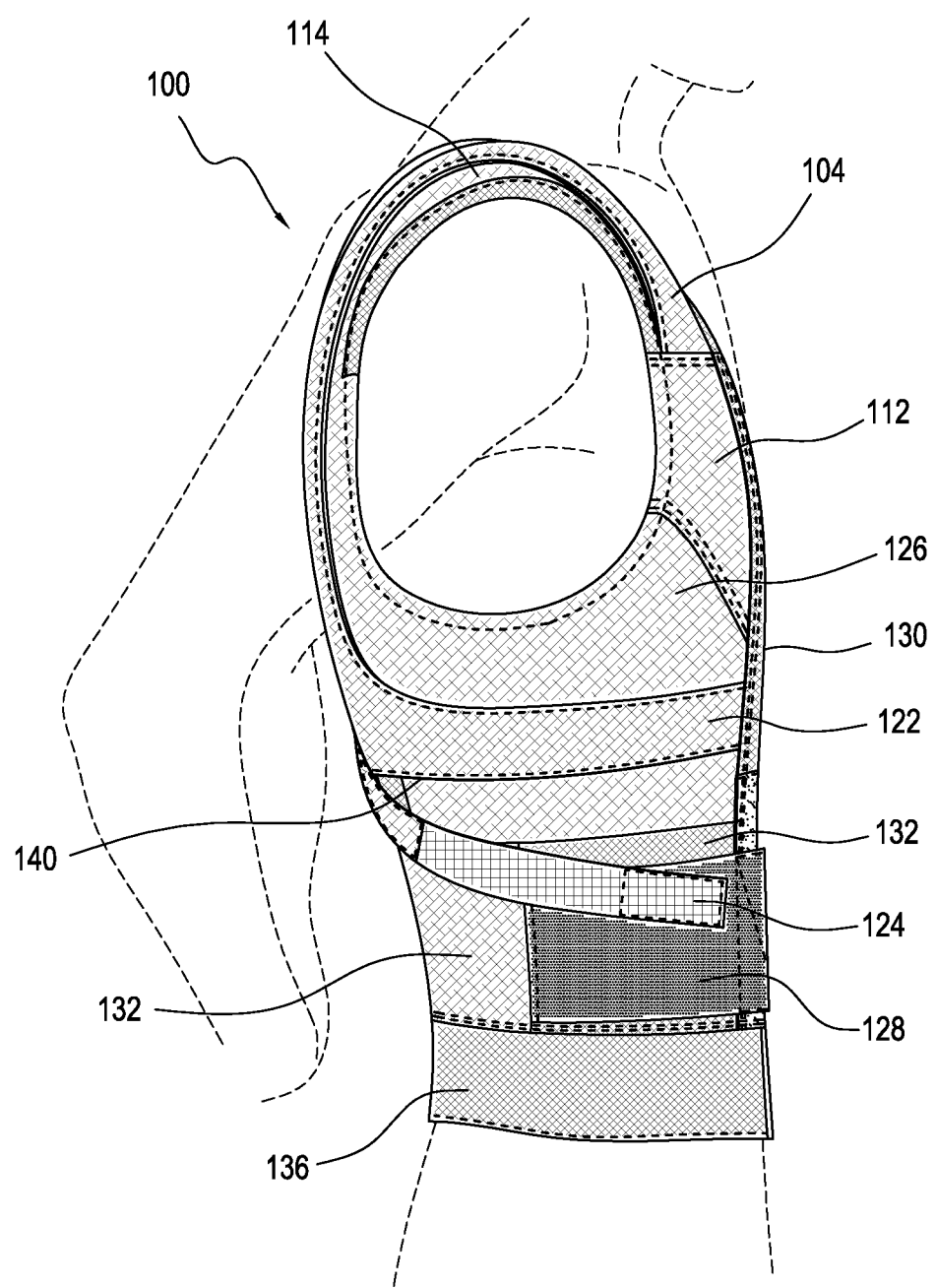
FIG. 2 is a side elevational view of the embodiment of the garment in FIG. 1.

The drawing figures are not drawn to scale, but instead are drawn to provide a better understanding of the components, and are not intended to be limiting in scope, but to provide exemplary illustrations.

DETAILED DESCRIPTION OF VARIOUS EMBODIMENTS

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

It will be understood that, unless a term is defined in this disclosure to possess a described meaning, there is no intent to limit the meaning of such term, either expressly or indirectly, beyond its plain or ordinary meaning.

Disclosed herein are embodiments of an orthopedic device for scapulothoracic stabilization, inclusive of features for biomechanical stabilization of the shoulder, scapula and spine, treated alone or in combination with assembly features for supporting an arm or shoulder. Whether as a garment or shoulder harness, the embodiments may be constructed from different textile materials that form panels having different elastic properties, or straps interconnected with one another. Lightweight and breathable frictional padding materials are employed to provide combined properties of friction and compressibility to enhance the properties of the textile-based panels and straps. Uniquely placed, structured and functioning straps may be added to enhance the textile materials and frictional padding materials to enable corrective action to a user without unobtrusive structural features and inhibiting migration of the vest over the user's body. The features of the orthopedic device improve stabilization of the shoulder, scapula and spine while offering a user with increased comfort and leads to increased user compliance.

The garment and shoulder harness both rely on similar principles in regard to how they aid scapulothoracic stabilization. Specifically, various straps form a "Figure 9" shape wrapping about the anterior side and extending to the posterior side of the shoulder to form a junction having a "Y" or bifurcated shape and used to anchor about the torso or waist of the user. Specifically, the garment or shoulder harness relies on the "Figure 9" system on the contra shoulder (relative to the injury) of the user to suspend a shoulder support such as a sling or brace assembly, or tighten thereabout. The Y-shape formation of the strap system extends from the contra shoulder. The garment and the shoulder harness enables scapular stabilization on the ipsilateral side (affected shoulder or side) to create scapular stabilization of the glenohumeral joint, preferably on the truncal side, and stabilizes the humeral side of the glenohumeral joint.

In the illustrative embodiment of FIGS. 1-6, a garment 100 includes a vest component 102 comprising a plurality of breathable panels having different elasticities and/or stiffness. The panels may be formed from different textiles, or formed from the same textile. First and second shoulder straps 104, 106 are secured to the vest component 102. The first and second shoulder straps 104, 106 have first and second anchor portions 120, 122 at the exterior surface 162 securing to the vest component 102, and a third anchor portion 124 removably securing to the vest component. The first and second shoulder straps 104, 106 form a "Figure 9" shape wrapping about the anterior side of the vest 102, extending to the posterior side of the vest 102 to form a junction having a "Y" or bifurcated shape and connecting to the third anchor portion 124. A waist stabilizer 107 having belt arms 108, 110 secure to the vest 102 and include first and second anchor portions 152, 153 securing to the vest component 102.

In any of the embodiments described herein, the belt arms or waist stabilizer can be arranged with a tensioning or pulley system similar to a lumbar belt or orthoses discussed in U.S. Pat. No. 8,172,779, granted on May 8, 2012, and pending U.S. application Ser. No. 15/053,247, filed on Feb. 25, 2016, and incorporated by reference.

An interior surface 164 includes anti-migration or frictional material segments 116, 117 corresponding to the first and second anchor portions 120, 122 of the first and second shoulder straps 104, 106. The frictional material has frictional properties greater than frictional properties of the textile forming the panels, and is preferably intended to engage skin of the user, although it may suitably engage other garments worn by the user to maintain the garment in place. The frictional material is breathable and has greater padding and compressibility properties than the panels comprising the vest 102. The frictional material may be the same as in U.S. application Ser. No. 14/996,065, filed on Jan. 14, 2016, and incorporated by reference in its entirety.

The vest 102 includes a spinal panel 140 spacing apart first and second shoulder panels 114, 115 corresponding to the first and second shoulder straps 104, 106. The spinal panel 140 is stretchable and elastic whereas the first and second shoulder panels 114, 115 are non-stretchable and substantially inelastic.

The first and second frictional material segments 116, 117 correspond to the first and second shoulder panels 114, 115, and are spaced apart by the spinal panel 140 to permit movement by the user. The shoulder straps 104, 106 preferably overlap both the shoulder panels 114, 115 and the frictional material segments 116, 117 such that pressure applies to the frictional material segments 116, 117 and creating greater friction against the user so the garment does not migrate over the shoulders when tension applies to the shoulder straps 104, 106.

The first anchor portion 120 is at an anterior side A of the vest 102 at an upper portion U corresponding to the first shoulder panel 114. The second anchor portion 122 is at the anterior side A of the garment at a middle portion M below the upper portion U and corresponding to the first shoulder panel 114. The first and second anchor portions 120, 122 are stitched to the first shoulder panel 114 to not separate from the garment during adjustment and tensioning of the first and second straps 104, 106.

A chest panel 112 is between upper and middle portions U, M of the first shoulder panel 114 on the anterior side A of the garment 100. The chest panel 112 has different stiffness properties than the shoulder panel 114 and may be inelastic or elastic. A central panel 130 extends between opposed sides of the shoulder panel 114 on the anterior side A of the garment 100.

Figure 4:
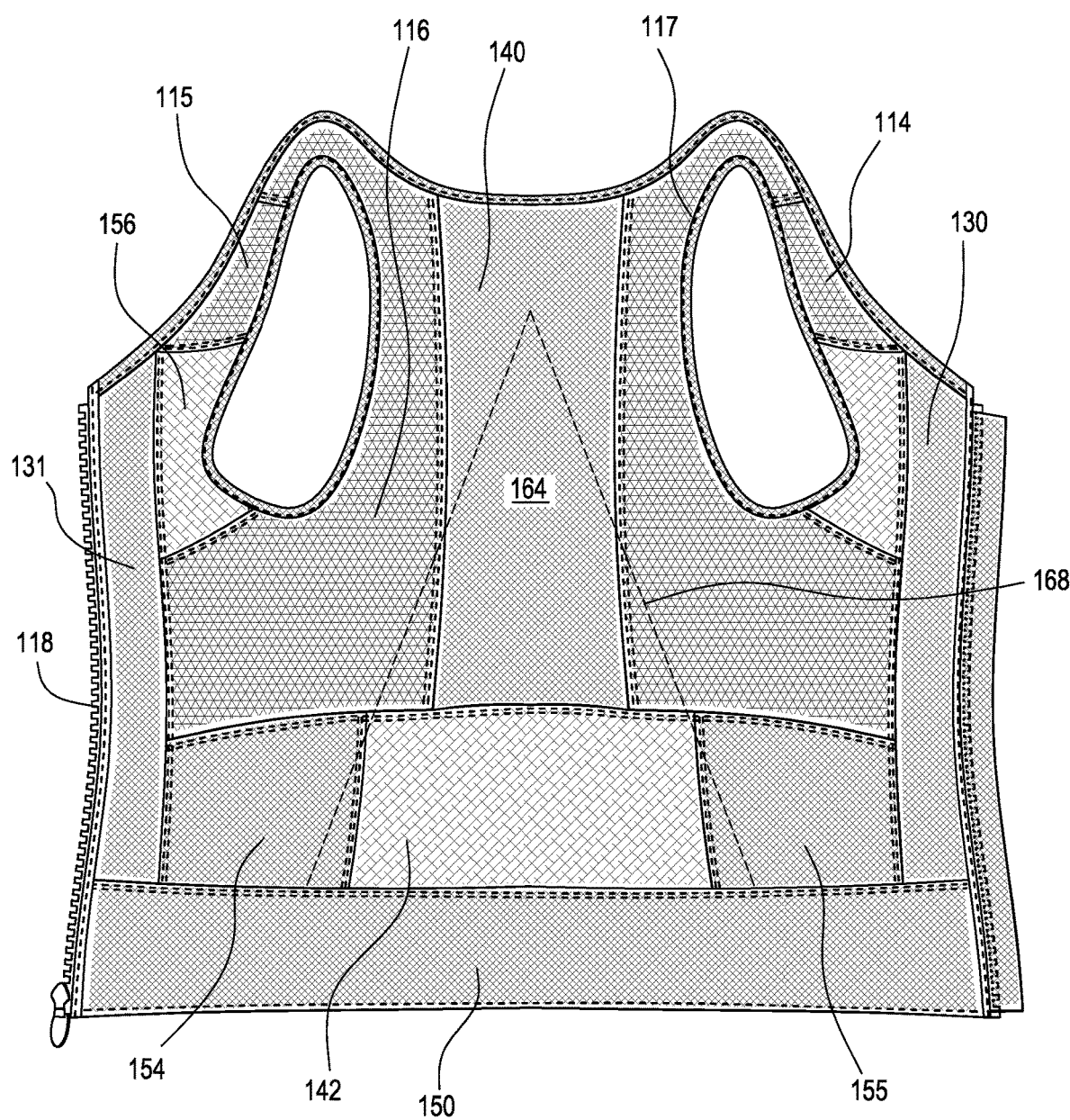
FIG. 4 is a front elevational view of the embodiment of the garment in FIG. 1 in an open configuration.
Figure 5:
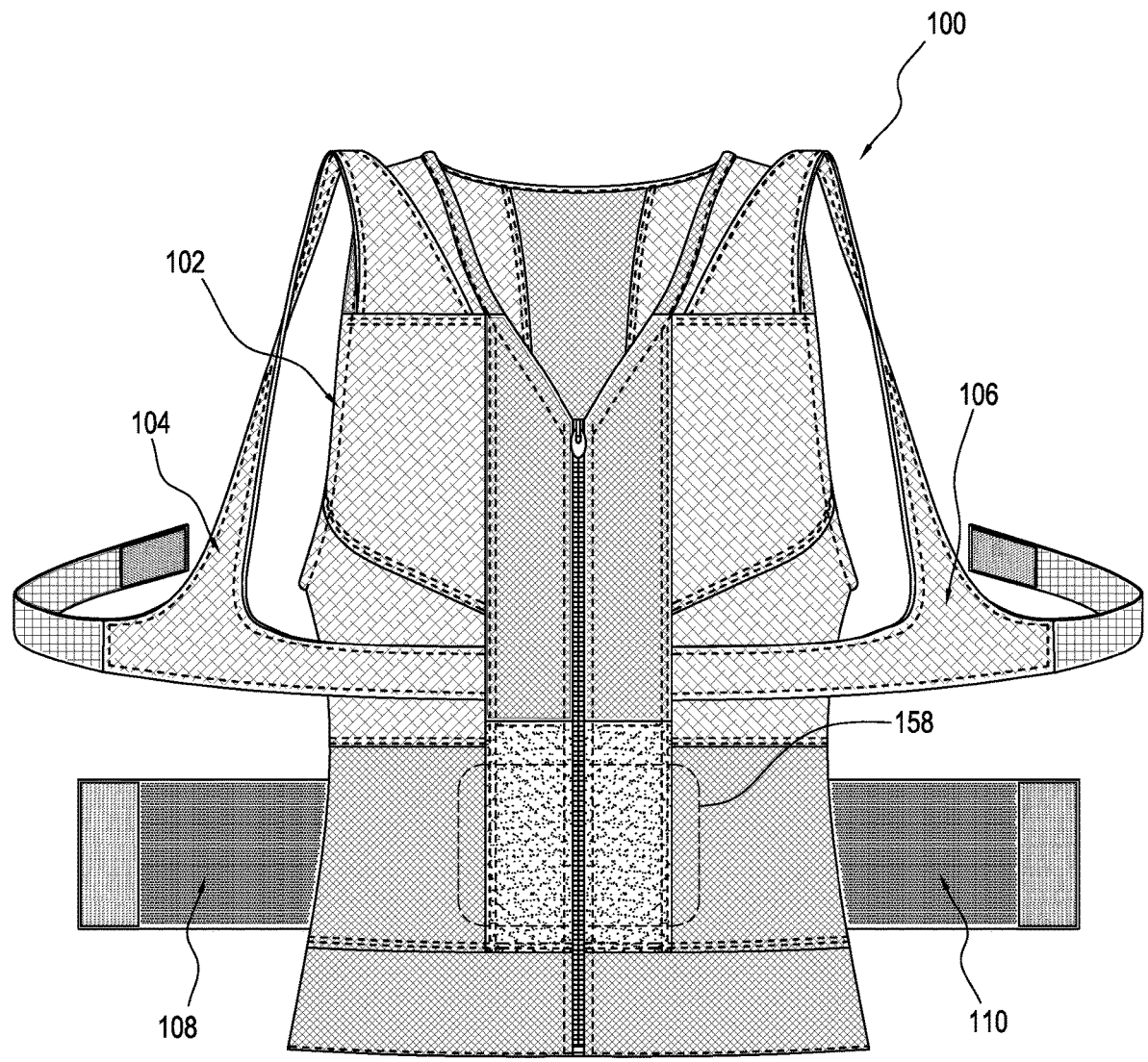
FIG. 5 is a front elevational view of the embodiment of the garment in FIG. 1 in a closed configuration without the shoulder straps and waist stabilizer secured.
Figure 6:
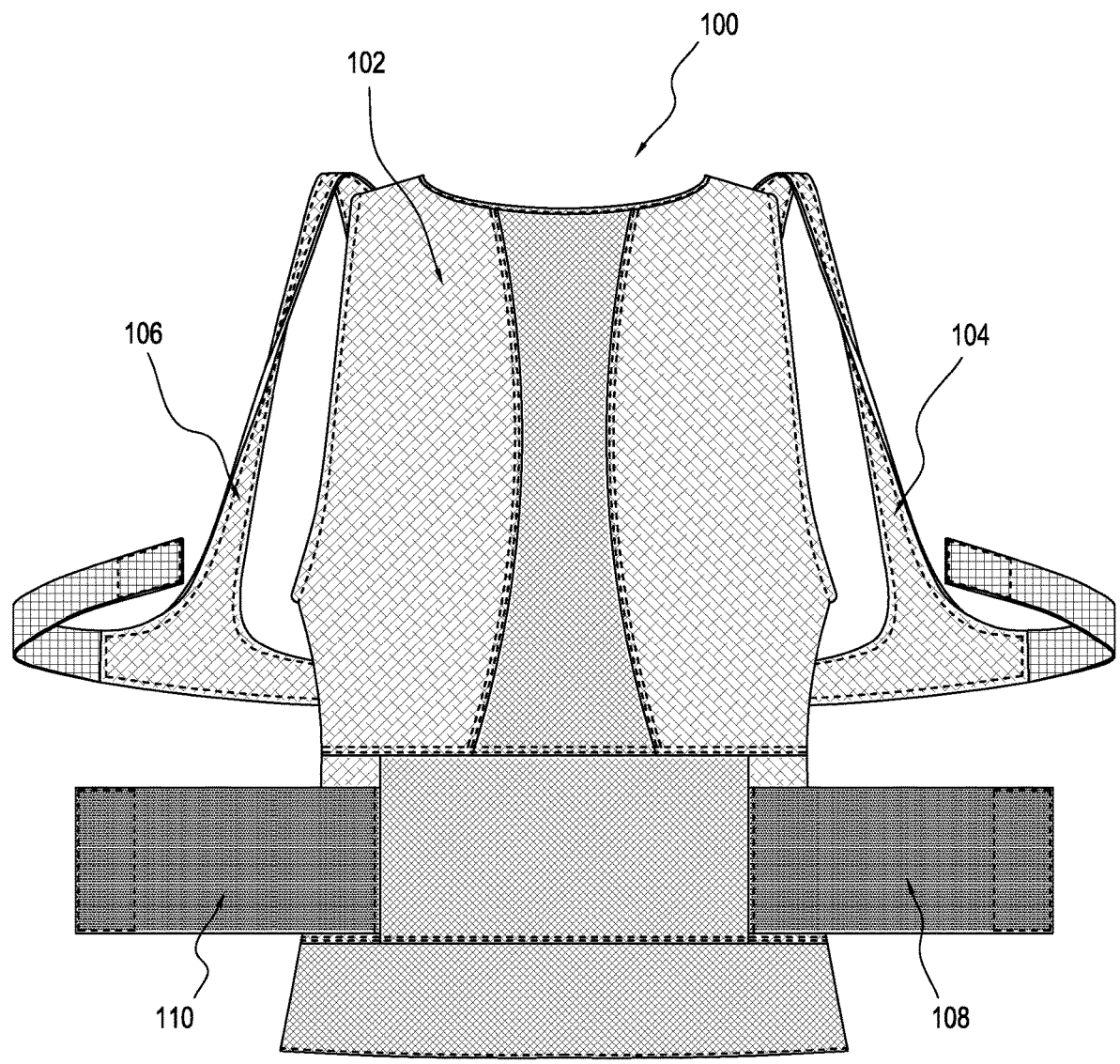
FIG. 6 is a rear elevational view of the embodiment of the garment in FIG. 2 in a closed configuration without the shoulder straps and waist stabilizer secured.

A closure 118 extends along the length of an anterior side A of the garment 100 for opening the garment 100. The closure 118 may extend the entire longitudinal length of the anterior side A of the vest 102, and opens the vest 102, as shown in FIG. 4. The closure 118 divides the central panel 130 into opposed sides, such as left and right sides of the user. The central panel 130 is substantially more stretchable than the first shoulder panel 114.

The first shoulder strap 114 includes a stretchable segment 144 carrying the third anchor portion 124 such that the remainder of the first shoulder strap 104 is substantially non-stretchable. The first and second anchor portions 120, 122 secure to the anterior side A of the garment and extend to a posterior side P of the garment 100 joining at a first junction 146 such that the stretchable segment 144 extends from the junction to enable the third anchor portion 124 to wrap about and secure to the anterior side A of the garment 100. The junction 146 forms a generally Y-shape with the first, second and third anchor portions 120, 122, 124 extending therefrom. The first junction 146 of the first shoulder strap 104 overlaps a second junction 148 formed by the second shoulder strap 106.

A rib panel 126 extends between the first and second anchor portions 120, 122 and forming part of the first shoulder panel 114. A sleeve 160 extends over and secured to the first shoulder panel 114 on the anterior side A of the garment 100 through which the first anchor portion 120 extends toward the posterior side P of the garment 100.

The spinal panel 140 is on the posterior side P of the garment 100 and extends across the upper and middle sections U, M of the garment 100. A rear panel 142 is below the spinal panel 140 such that the spinal panel 140 is substantially more flexible than the rear panel 142, which may be inelastic.

First and second waist panels 154, 155 are on opposed lateral sides of the rear panel 142 and are substantially more elastic than the rear panel 142. A tail panel 150 extends at least from and downwardly toward the lower portion of the garment 100 from the first and second waist panels 154, 155 and the rear panel 142. The tail panel 150 may extend substantially more from the posterior side P than the anterior side A to enable a wearer to tuck in the tail panel 150 into pants. The tail panel 150 may be substantially elastic and thinner than the rear panel 142.

The waist stabilizer 107 includes first and second belt arms 108, 110 formed as belt segments having first and second anchor portions 152, 153, respectively, securing to a posterior portion P of the garment 100. The first and second anchor portions 152, 153 are preferably spaced apart by the rear panel 142 which may be substantially inelastic. The first and second belt arms 108, 110 are preferably elastic. In this embodiment, the belt arms 108, 110 are preferably stitched at the first and second anchor portions 152, 153 to the rear panel 142. Alternative arrangements may be employed in which the waist stabilizer 107 is a separate lumbar belt known in the art of orthopedic devices.

According to the illustrated embodiment, the first and second belt arms 108, 110 have forward ends 128, 129, respectively, securing to a pad section 138 at an anterior side A generally at a lower portion L of the garment 100. The pad section 138 may be substantially inelastic, although a variation may permit semi-elasticity to enable movement by the user at the waist. The first shoulder strap 104 includes a tab 132 carried by the third anchor portion and secures to an outer surface 166 of the belt arms 108, 110.

Figure 3:
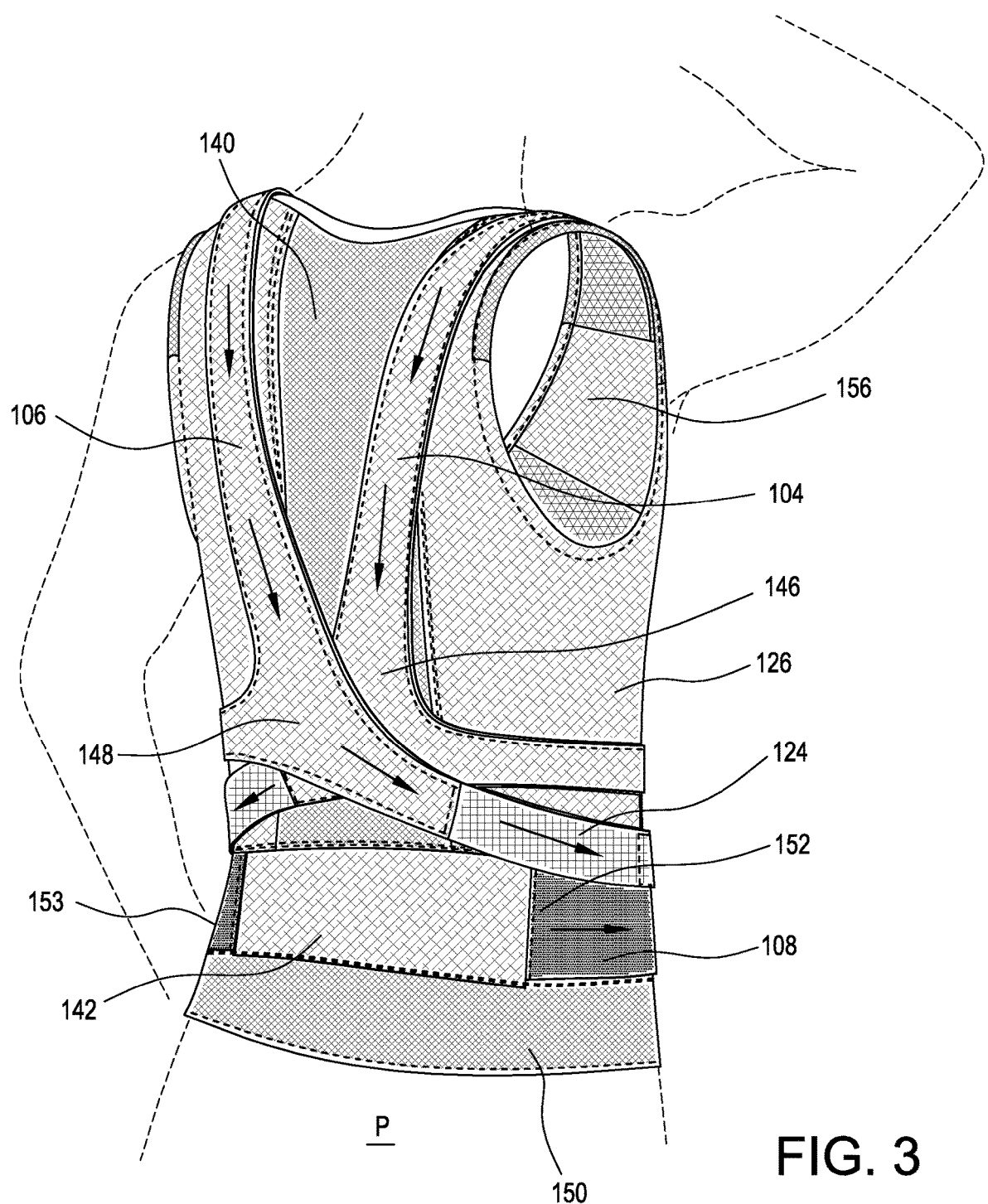
FIG. 3 is a posterior perspective view of the embodiment of the garment in FIG. 1.
Figure 9:
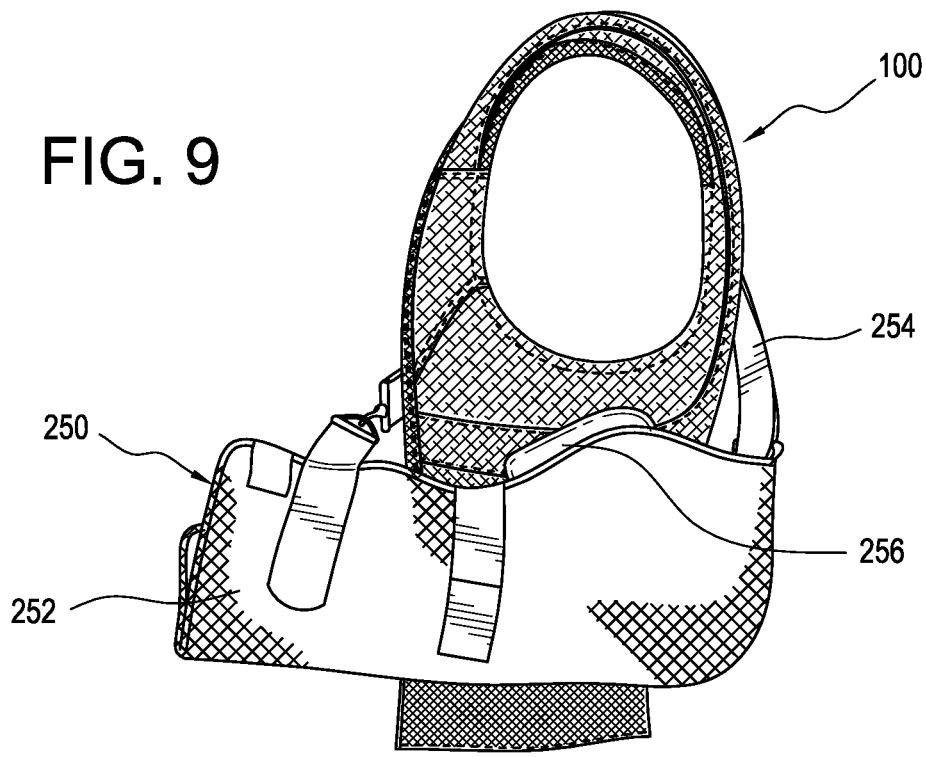
FIG. 9 is a side elevational view showing the garment of FIG. 1 in combination with a shoulder sling.

As shown by arrows on the first and second shoulder straps 104, 106 in FIG. 3, the first and second shoulder straps 104, 106 form the "Figure 9" configuration, and are tensioned from the first and second anchor portions on the anterior side A of the vest 102 to wrap about the posterior side P of the vest 102, and secure at the third anchor portion 124 over the waist stabilizer 107.

The vest 102 may be provided with an anterior plate 158 removably securing to a pad section 138 located a lower portion L along the anterior side A of the garment 100. In this embodiment, the belt arms 108, 110 are tensioned over the anterior plate 158, and the forward ends of the belt arms 108, 110 may secure to fastening means on the anterior plate 158. The tab 132 of the first shoulder strap 104 carried by the third anchor portion 124 secures over the forward end 128, 129 of the waist stabilizer 107 to further compress the anterior plate 158 over the user. The anterior plate may be substantially rigid.

The garment 100 may include a posterior plate securable to at least the rear panel 142 on the interior side 164 of the garment 100 to provide lumbar compression. The posterior plate 168 may be substantially rigid. The anterior and posterior plates may be made according to the embodiments discussed in U.S. pending application publication 2014/0081189, published Mar. 20, 2014, and incorporated herein by reference.

The fastener means by which the components of the garment removably secure to one another such as the shoulder straps, belt arms, and anterior and posterior panels, may include mutually cooperating fasteners such as hook-and-loop system, hooks, buttons and other known means used for fastening articles. Likewise, the closure may be a zipper or any of the aforementioned fastener means.

According to a method for applying the garment to a user, the garment may be laid down with the closure opened for donning the vest, with the waist stabilizer and corresponding shoulder straps. The posterior panel may be affixed to the interior of the vest and the contour of the posterior panel should be oriented to create support in the lumbar region of the back.

The vest is placed over the user, with arms being inserted through arm holes 170, 172, with the neck opening 174 permitting extension of a neck of the user and the trunk opening 176 at or above a user's waist. The closure is closed according to its construction. The garment is preferably worn against a user's skin to enable the frictional material to grip the user's skin; however, the garment may be worn over clothing.

The anterior plate is preferably affixed to the pad section by centering the anterior plate over the pad section and the closure at the lower abdomen of the user. The belt arms are tensioned and secured to either the pad section or over the anterior plate which may include fastening means. The belt arms are snugly fastened to the anterior plate or pad section at the abdominal region of the user. The user is encouraged exhale at the abdomen and position the shoulders in an upright position with the shoulders rolled back and down. The shoulder straps are grasped with the third anchor ends being directed to the abdomen on the anterior side of the user until the shoulder straps maintain the user's posture in a proper and upright manner with comfortable tension in the straps.

Figure 7:
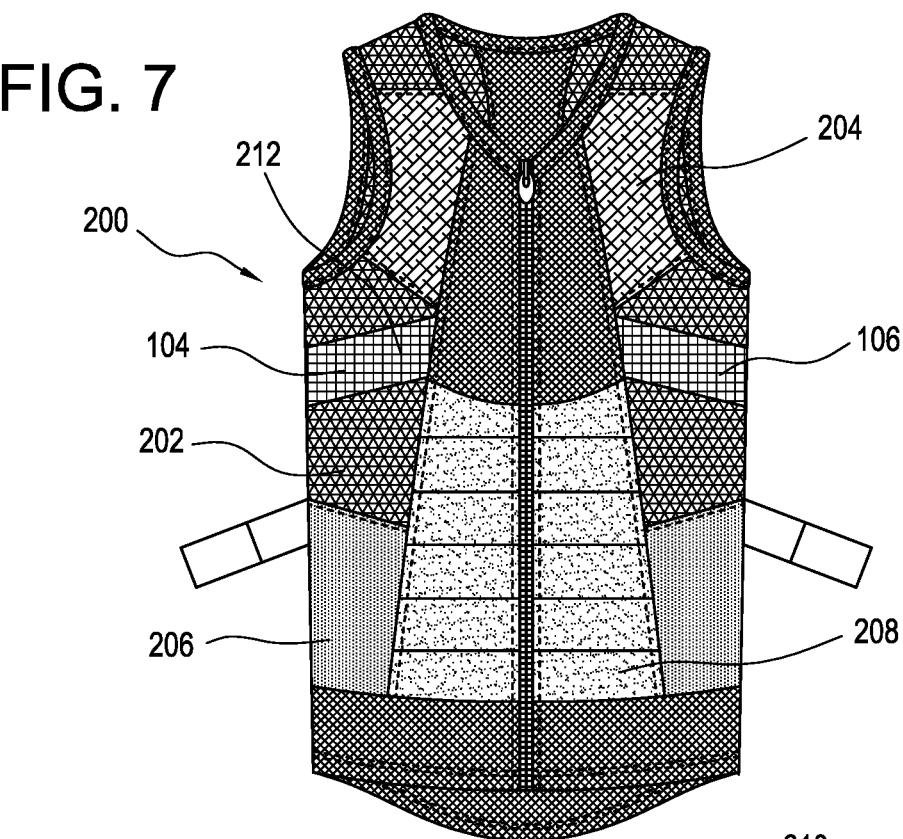
FIG. 7 is a front elevational view of a variation embodiment of the garment in FIG. 1 in closed configuration.
Figure 8:
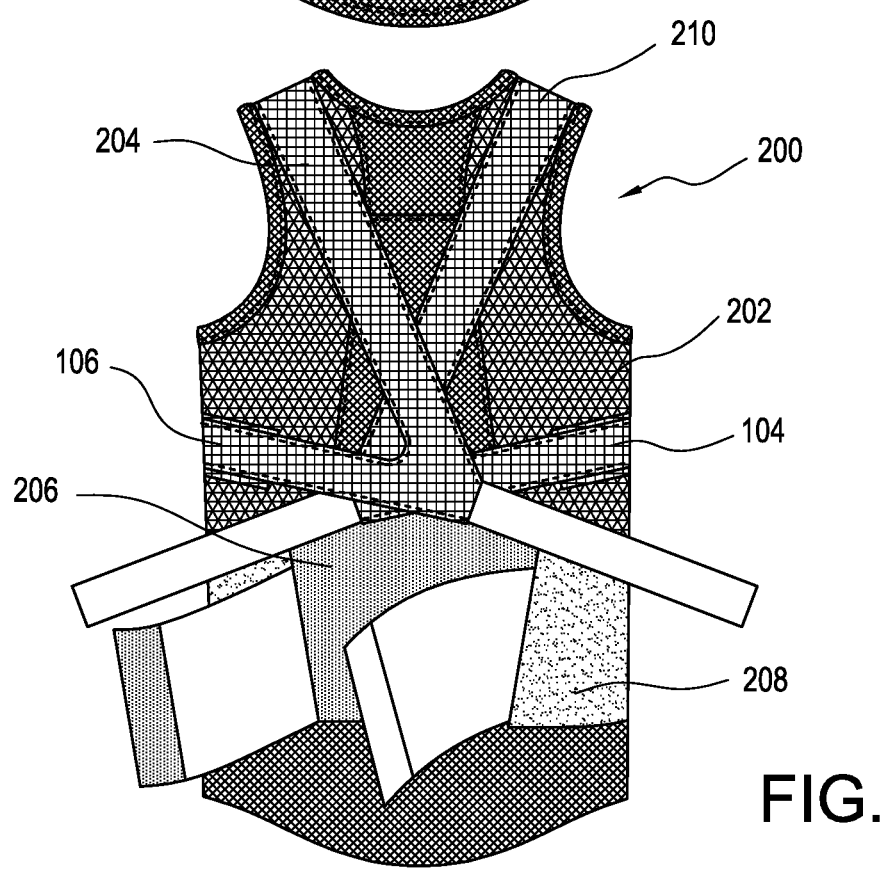
FIG. 8 is a rear elevational view of a variation embodiment of the garment in FIG. 7.

According to the variations of the garment 200 in FIGS. 7 and 8, panels 202, 204, 206, 208 are illustrated as having different stretch, absorbent and fastener properties. The combination of the different properties of the panels and their arrangement relative to one another enable the straps and connection sections to form the "Figure 9" configuration integrated into the garment 200.

The first panel 202 is formed from a non-stretchable material or absorbent material or combination of both. The first panel 202 is arranged for providing a tactical grip zone over the surface of the user, such as the user's skin to assist with traction of the garment on the user. The first panel 202 is preferably provided in combination with the frictional material discussed above located on the interior surface of the garment. As the frictional material is breathable, the first panel 202 is likewise breathable to move moisture away from the user's body as the first panel 202 grips the user's body. The absorbent material may be arranged in a large surface area to react with the user's skin, thus spreading forces applied by the straps across a larger area.

The first panel preferably provides additional support at both anterior and posterior areas of the garment. The first panel may comprise a single material having both the non-stretchable and absorbent properties, or alternatively may comprise multiple layers having non-stretchable and absorbent properties. A layer of absorbent material may be laminated or coat a non-stretchable layer.

The second panel 204 is formed from a non-stretchable material. The second panel 204 is arranged to adjoin the first panel 202 or with the straps 104, 106, extend over the first panel 202. The straps 104, 106 may be ridged, and connected to the garment at the clavicle and serratus areas 210, 212.

The third panel 206 is formed from a non-stretchable material having an unbroken loop material on the exterior surface. The third panel 206 provides a ridged non-stretch anterior and posterior area for an elastic lumbar belt to secure and pull against, including an integrated support. The third panel 206 forms attachment areas for belts, strap, and additional components such as plates and arm slings. The fourth panel 208 is formed from a stretchable material. The material is stretchable to provide for an intimate fit, and provides moisture wicking to pull moisture away from the body. As with the first panel, the other panels may comprise a single layer having the specified properties or comprise a plurality of layers having properties to achieve the aforementioned general properties of the panels.

Figure 10:
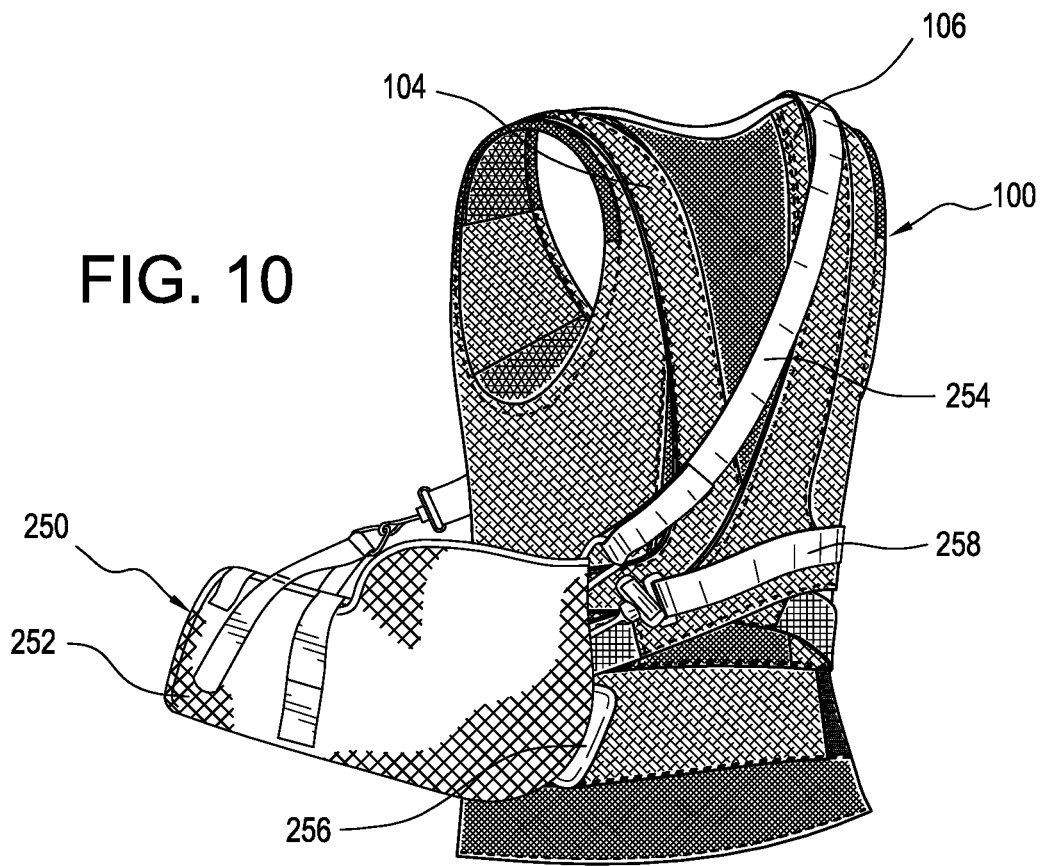
FIG. 10 is a rear perspective view showing the garment and shoulder sling combination of FIG. 9.

FIGS. 9 and 10 exemplify usage of a shoulder or arm support 250, such as a sling, in combination with the garment for post-operative treatment of a shoulder. The combination of the shoulder sling provides stabilization of the forearm/arm glenohumeral joint in all three planes (sagittal for flexion/extension; coronal for abduction/adduction; and transverse for rotational). The shoulder sling 250 includes a shoulder strap 254 that extends around the unaffected shoulder, a waist strap 258 and an arm sleeve 252. A bolster 256 may be provided to prop the arm at an angle relative to the waist or shoulder.

In the following embodiments, the orthopedic device is embodied as a shoulder harness relying on similar principles to the aforementioned garment embodiments. Specifically, the shoulder harness relies on the "Figure 9" system on the contra shoulder (relative to the injury) to suspend a sling or brace assembly. The shoulder harness likewise employs a generally Y-shape formation of at least the strap system extending from the contra shoulder. The shoulder harness enables scapular stabilization on the ipsilateral side (affected shoulder or side) to create scapular stabilization of the glenohumeral joint, preferably on the truncal side, and stabilizes the humeral side of the glenohumeral joint.

Figure 11:
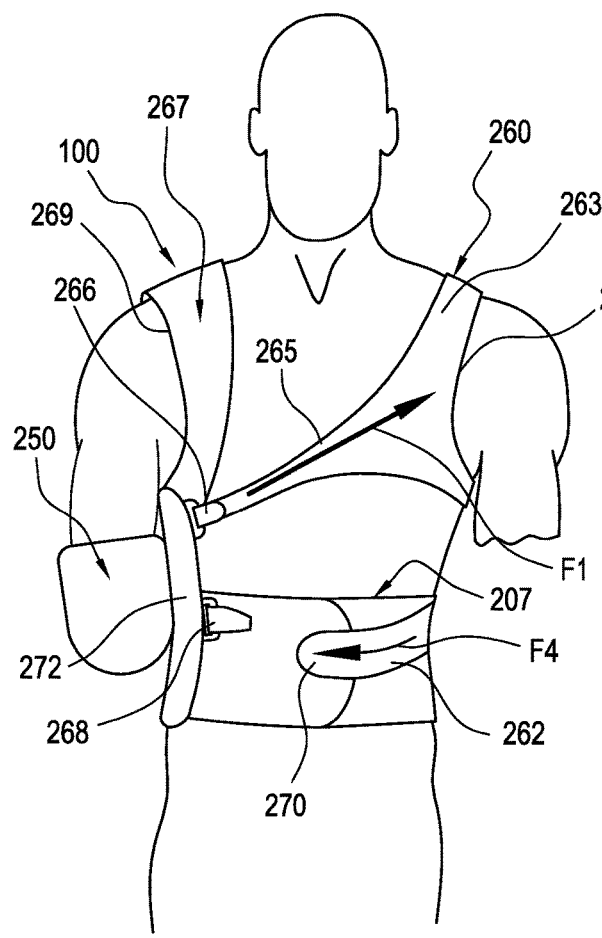
FIG. 11 is a front perspective view of another embodiment the orthopedic device for scapulothoracic stabilization in the form of a shoulder harness relying on similar principles as the garment of FIG. 1 in combination with an assembly feature in the form of a sling attachment.
Figure 12:
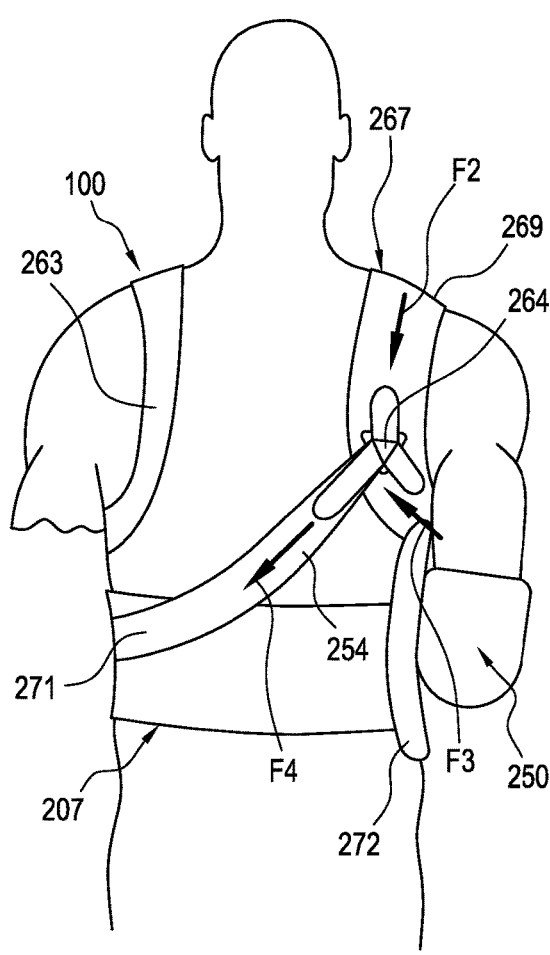
FIG. 12 is a rear perspective view of the shoulder harness with a sling attachment of FIG. 11.

The shoulder harness may be employed with a sling, such as a sling attached to a waist, as with the embodiments of FIGS. 11 and 12, or with a shoulder brace, as in FIGS. 13-16. The shoulder harness in combination with a shoulder support, such as a sling or shoulder brace, may be used to place the shoulder and brace assembly in positions including gunslinger, neutral plane and external rotation. Because of the adjustability, the shoulder harness and brace assembly can accommodate various user sizes and anatomies. The shoulder harness is arranged to relieve pressure on the user's neck by the arrangement of counteracting strap assemblies.

FIGS. 11 and 12 exemplify a shoulder harness 260 arranged for carrying a shoulder or arm sling 250 (schematically shown), and providing adjustable scapular stabilization. The shoulder harness 260 may be used in combination with the aforementioned garment or similar garment, as schematically shown in FIGS. 11 and 12, or by itself. The shoulder harness 260 includes a first strap system 261 having a first component 263 extending about and over the shoulder and under the arm, and in the event worn with a garment, generally over one of the shoulder straps 104, 106 of the garment 100 of FIG. 1. The first strap system 261 also has a second component 265 extending from the first component 263 across an anterior side of the garment or chest of a user to the shoulder or arm sling 250, preferably by a lateral support 272 to adjustably attach to the shoulder or arm sling 250 by a connection 266.

The first strap system 261 generally forms the "Figure 9" configuration as in the preceding embodiments, and provides a solution as an additional or stand-alone component for stabilizing the shoulder, whether or not provided in combination with the garment. The first and second components 263, 265 of the first strap system 261 forms a "Y" shape extending over the anterior of the side of the user and hence garment, with the first component fully encircling the shoulder, for reasons discussed in connection with preceding embodiments.

A second strap system 267 has a first strap 269 generally encircling the affected shoulder and secures to a second strap at a junction 264 on the posterior side of the user. The junction 264 may comprise brackets, D-ring, or attachments, such as hook and loop, for adjustably securing the first strap 269 to the second strap 271, in part for sizing to the anatomy of the user. The second strap 262 extends from the junction 264 across the posterior side of the user to adjustably secure to the waist or torso stabilizer 207, either provided with the garment or a separate waist stabilizer, such as a lumbar belt discussed above. Alternatively, the end 270 of the second strap 262 may adjustably secure to the shoulder or arm sling 250 by another connection 268 (as shown by the dashed line) to the lateral support 272.

The shoulder harness with the aforementioned features according to the embodiment of FIG. 1 and modifications thereof advantageously stabilize the affected shoulder's scapula thus providing proximal stabilization of the glenohumeral joint. The shoulder harness provides stabilization of the shoulder sling so weight of the affected arm is not suspended from a strap about the neck but is suspended by hanging around the entire opposite shoulder. The waist stabilizer may have ample hook receivable material or unbroken or loop material. This provides the ability to affix a lateral support 272 such as a bolster, lateral paddle or plate, such as one being malleable, rigid or semi-rigid, to the side of the thorax or waist. This provides proper arm/glenohumeral positioning and takes the weight of the arm. For example, the first component 263 forms a "Figure 9" about the contralateral shoulder from the lateral support. The lateral support 272 is attached to the waist stabilizer 207 and to the "Figure 9" configuration, creating suspension of the lateral support, shoulder joint/forearm assembly.

As shown in FIGS. 11 and 12, the first strap system 260 exerts a first force F1 component toward the shoulder about which it extends from the shoulder or arm sling 250 to suspend the shoulder sling on the contra shoulder relative to the injured shoulder. The second strap system 263 serves as the scapular stabilization portion of the shoulder harness as it divides into second and third components F2, F3 over and under the shoulder to the junction 264, the combination of F2 (depression of the scapula) and of F3 (adduction of the scapula). A fourth force component F4 extends along the second strap 262 to the point whereat the end 270 secures. The line of pull is adjusted to optimally create F2 and F3 by the adjustable attachment or junction 264. The resultant force F4 is applied by the second strap 262 and secured into position by a fastener to the waist stabilizer 207.

In summary, the first strap system 260 on the contra shoulder suspends the shoulder sling, whereas the second strap system on the ipsilateral side (affected shoulder), creates scapular stabilization of the glenohumeral joint (on the truncal side of the glenohumeral joint). The shoulder harness stabilizes the humeral side of the glenohumeral joint.

According to FIGS. 13-16, basic principles of the aforementioned garment and shoulder harness may be applied to a shoulder brace. The shoulder brace in combination with the shoulder harness, as in the embodiment of FIGS. 11 and 12, is arranged to immobilize the shoulder for non-surgical or post-op shoulder conditions, and post injury rehabilitation requiring a user's arm to be positioned in a fixed configuration. The shoulder harness may be used with or without the aforementioned garment, but still relies on the "Figure 9" configuration and the generally Y-shape formation of the straps.

The shoulder brace 300 includes a shoulder harness 301 and a support assembly 302 connecting to the shoulder harness 301 for suspending an arm and shoulder in a desired configuration. A torso or waist stabilizer 304, such as one discussed above, couples to both the shoulder harness 301 and the support assembly 302, and serves as an anchor for the shoulder harness 301 and shoulder support about the waist of a user.

The shoulder harness 301 includes a first strap system 303 having a first portion 306 arranged to encircle the shoulder of the user. The first portion 306 may be adjustable in size, such as with a buckle, bracket and/or suitable fastener, so that it can accommodate different shoulder sizes. The first strap system 303 includes an anterior portion 308 extending obliquely or slanting from the first portion 306 about an anterior side A of a user to fasten to an anterior side of a lateral support 314 supporting a frame assembly 317 of the support assembly 302. The first strap system 303 has a posterior portion 309 extending obliquely or slanting from the first portion 306 about a posterior side P of a user to fasten to a posterior side of the lateral support 314 located on an opposite side of the user (i.e., left or right) as the first portion 306. Both the anterior and posterior portions 308, 309, form a "Figure 9" configuration with the first portion 306, and secure about the shoulder as in the foregoing embodiments.

The lateral support 314 is affixed to the waist stabilizer 304 by way of a fastener for forming the foundation or base of the securement effectively to the body. Attachments 353, 354 together serve to support the moments created by the cantilever forces created by the forearm/hand extending anteriorly from midline and the elbow/forearm extending laterally from the body. This securement may also require additional attachment from a lower post 324 of the support assembly 302 to the shoulder harness 301.

Both the anterior and posterior portions 308, 309 of the first strap system 303 fasten to the lateral support 314 by the attachments, such as brackets, 353, 354 having a catch or pin 316, adapted to releasably secure to the lateral support 314 by an opening 318 sized and configured for receiving the pin or catch 316. The anterior and posterior portions 308, 309 are thereby anchored to the lateral support 314 by the brackets 353, 354, and hence permit tensioning about the user by their attachment to the brackets 353, 354. The catch 316 enables the first strap system 303 to be sized in a set arrangement, and easily released from the lateral support 314, rather than resizing a length of the anterior and posterior portions.

Figure 13:
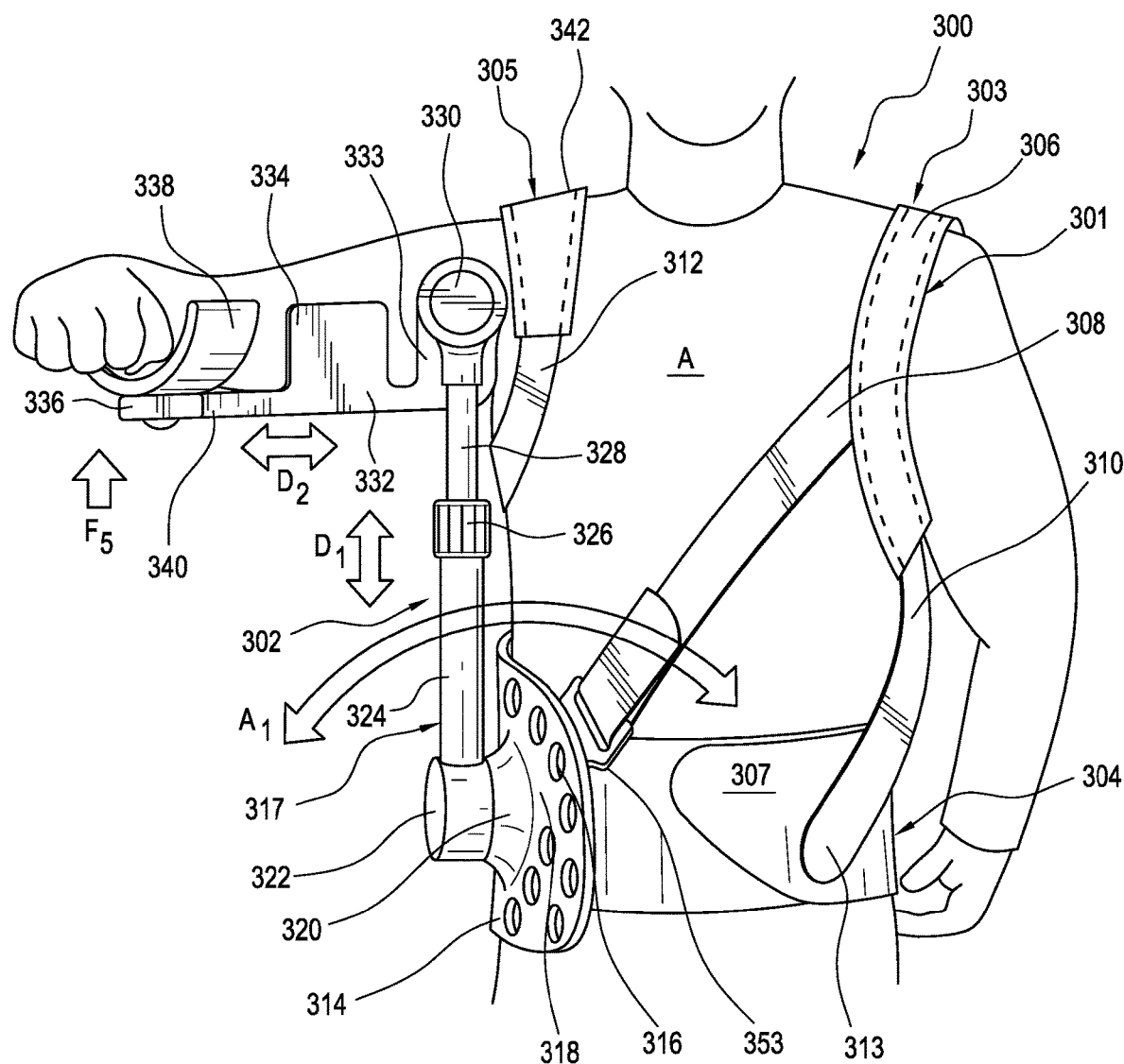
FIG. 13 is a front perspective view showing another shoulder harness embodiment with an assembly feature in the form of a shoulder brace.
Figure 15:
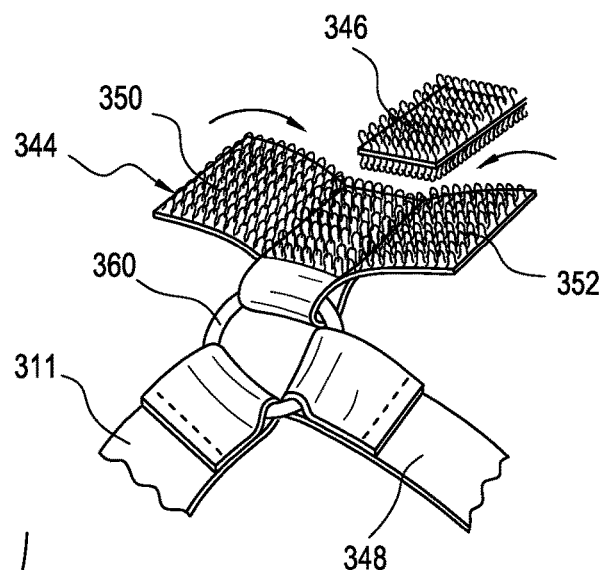
FIG. 15 is a perspective view of an attachment of a strap in the shoulder harness of FIG. 13.
Figure 14:
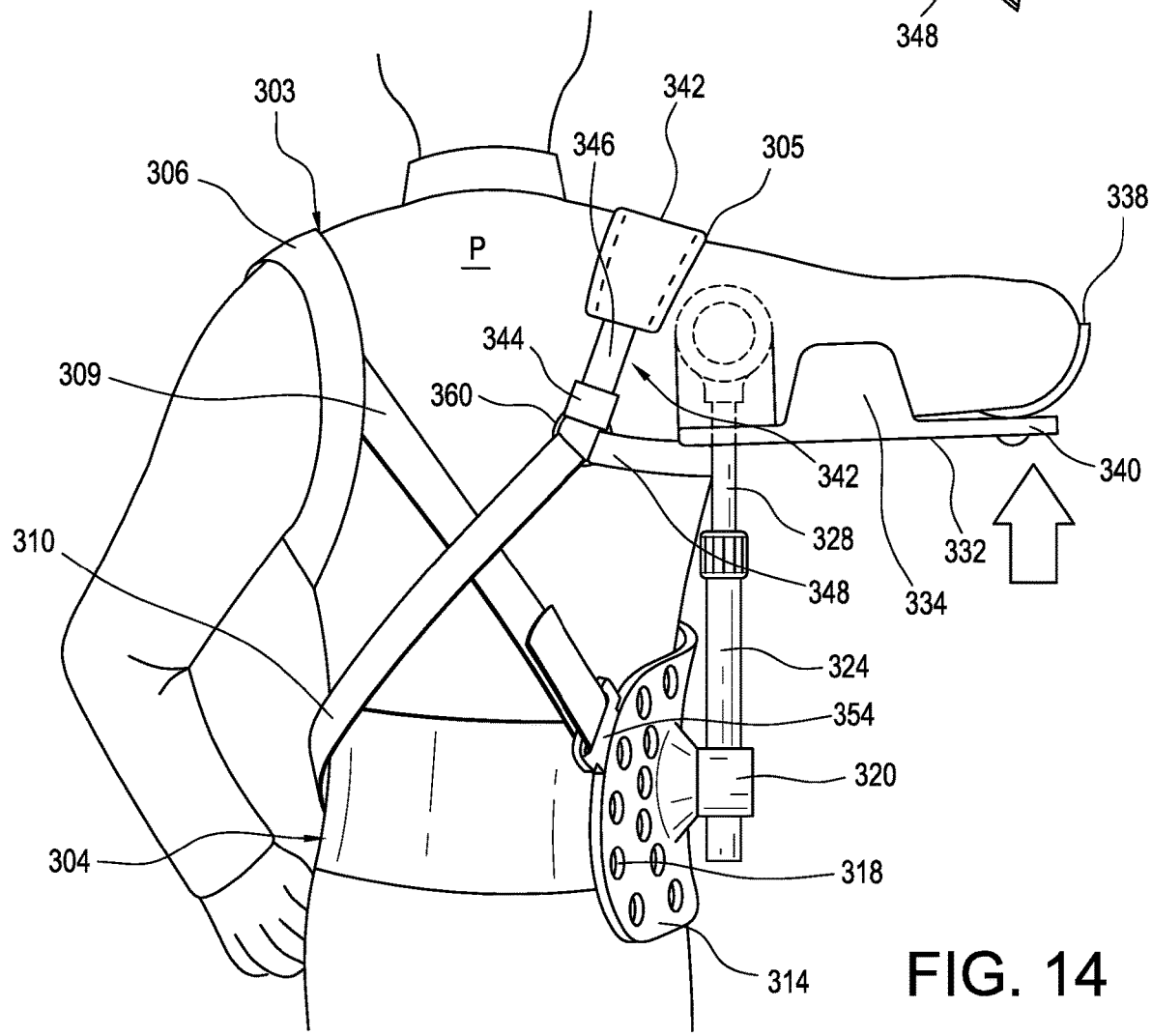
FIG. 14 is a rear perspective view showing the shoulder harness embodiment of FIG. 13.
Figure 16:
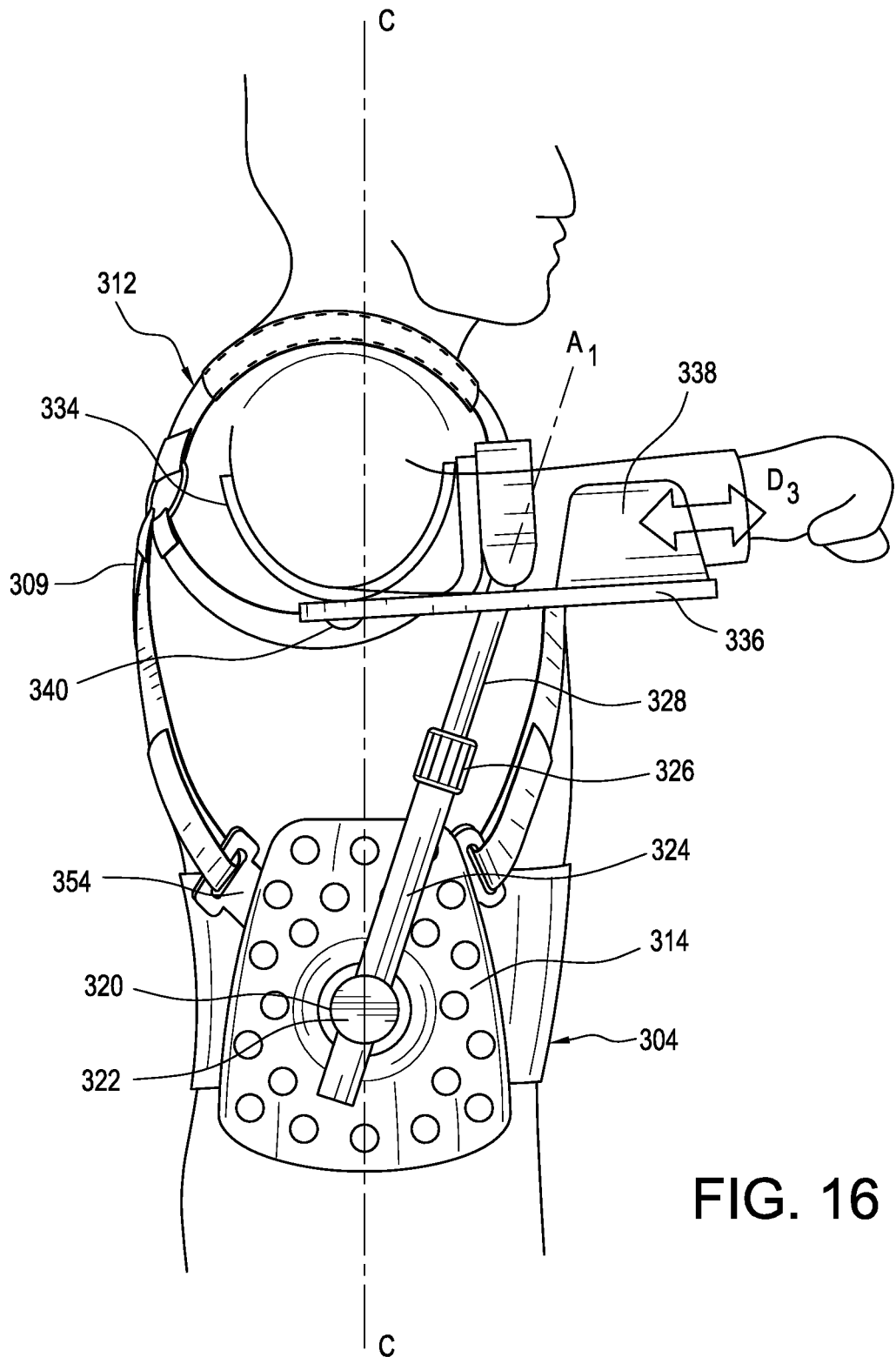
FIG. 16 is a side perspective view of the shoulder harness of FIG. 13.

The lateral support 314 may define a plurality of openings 318 at which the catch 316 can selectively engage to adjust the length and angle of the anterior and posterior portions 308, 309 relative to the opposed shoulder about which the first portion 306 extends. For example, as depicted in FIG. 13, the openings 318 extend about the periphery of the lateral support 314 at predetermined increments according to different angles relative to the user's shoulder for securing the anterior portion to the lateral support 314. A similar arrangement is shown in FIG. 14 with the plurality of openings 318 extending about the periphery of the lateral support 314 according to predetermined angles for receiving the posterior portion 309.

The lateral support 314 may be a rigid or semi-rigid plate contourable to a user's anatomy or provided in a set of predetermined shapes. For example, the plate may be cold-formable aluminum, or a plastic that can be reshaped to a user's specific anatomy. The lateral support 314 may have fasteners securable to a surface 307 of the torso stabilizer 304, such as in a hook-and-loop system, buttons, clips or other suitable fastener system to maintain placement of the lateral support to the torso stabilizer.

The shoulder harness 301 has a second strap system 305 adapted to secure about an opposed shoulder as the first strap system 303, and preferably about the treated shoulder upon which the support assembly 302 is used. The second strap system 305 includes a first strap 310 securing to a junction 360, such as a ring, on the posterior shoulder of the user, and a second strap 312 which secures to the junction 360 and extends about the treated shoulder. The first and second straps 310, 312 may discontinuous relative to one another in that they are discretely separated straps secured to one another by the junction 360 to form part of the second strap system 305.

The first end 311 of the first strap 310 engages the junction 360 at the posterior shoulder of the user and the first strap 310 extends therefrom wrapping about the waist on a side opposite to where the lateral support 314 is secured. The first strap 310 intersects the posterior portion 309 of the first strap system 303 over the posterior side P of the user. A second end 313 of the first strap 310 engages the surface of the torso stabilizer 304 by a suitable fastener, such as by hook-and-loop, generally on the anterior side A of the user. To remove the second strap system 305, the user can disengage the second end 313 of the first strap 310 from the torso stabilizer 304, and slide the second strap 312 over the arm.

The second strap 312 generally encircles the treated shoulder with a shoulder pad 342 arranged over the shoulder for additional padding for distributing pressure, and has first and second ends 346, 348 connecting to the junction 360. The first end 346 is preferably readily removable from the junction 360 by a sleeve 344 secured to the junction 360. The sleeve 344 is openable and has first and second flaps 350, 352 which engage the first end 346 of the second strap 312 to maintain it therewith. The flaps 350, 352 and the first end 346 preferably have a fastener system, such hook-and-loop, that enable the first end 346 to be readily removable from the junction 360 without destroying or adversely modifying the connection to the junction 360. The first end 311 of the first strap 310 and the second end 348 of the second strap 312 may be semi-permanently secured to the junction, such as by stitches, which would result in adversely modifying the first end 311 and second end 348 if removed from the junction 360.

The support assembly 302 is arranged for allowing internal/external rotation, abduction/adduction control, and flexion/extension control. In the embodiment of FIGS. 13-16, the support assembly 302 includes a lower post 324 received by a mount 322 on a pivot joint 320 secured to the lateral support 314. The pivot joint 320 is arranged for rotating and being locked in a plurality of angles, to thereby position the lower post 324 among a plurality of angles $A_1$ relative to a coronal plane C of the user for selecting a desired angle of the arm. A first end of an upper post 328 is telescopically received by the lower post 324 to vary the length $D_1$ of the combination of the lower and upper posts 324, 328, and locked relative to one another by a locking ring 326.

A second end of the upper post 328 is secured to a swivel joint 330 that is adjustable and spring loaded to maintain the shoulder in a fixed position. The swivel joint 330 preferably includes a spring, such as a coil spring, to urge and suspend the arm in a fixed and selective position relative to the user's shoulder. In the depicted embodiment, the swivel joint 330 is preferably located on the anterior side of the shoulder since preferably the arm will be directed toward and away from the anterior shoulder of the user. The swivel joint 330 rigidly suspends the user's arm, and the spring urges a force $F_5$ that resists the weight of the user's arm.

The swivel joint 330 is connected to a first strut 332 adapted to telescope and have its length selectively regulated and locked to a distance $D_2$ according to a length of a user's upper arm between the elbow and armpit. The first strut 332 may be shaped or an L-shaped bracket 333 may connect the first strut 332 to the swivel joint 330. The first strut 332 carries a first cuff 334 arranged to support the upper arm. The first strut 332 secures to a hinge 340 pivotally connecting to a second strut 336 carrying a second cuff 338 supporting a forearm. The hinge 340 is arranged to generally correspond to a user's elbow, and the second strut 336 is likewise arranged to telescope to accommodate a length or distance $D_3$ of a user's forearm.

The combination of the shoulder support, interchangeably embracing herein shoulder or arm slings and brace assemblies as noted in combination with the embodiment of FIGS. 13-16, and the shoulder harness enables positioning and supporting the shoulder post operatively as this allows for stabilization across the joint including scapula to thorax and humerous to scapula.

While the foregoing embodiments have been described and shown, alternatives and modifications of these embodiments, such as those suggested by others may be made to fall within the scope of the invention. While the orthopedic device has been discussed in the context of scapulothoracic stabilization and generally treating a shoulder, it will be understood that the principles described may be extended to other types of orthopedic and prosthetic devices.

Reference characters are provided in the claims for explanatory purposes only and are not intended to limit the scope of the claims or restrict each claim limitation to the element shown in the drawings and identified by the reference character.

The invention claimed is:

1. A shoulder harness adapted to secure to a sling on a first lateral side of a user, the shoulder harness comprising:
 a first strap system having a first component arranged to extend about a second or contralateral shoulder of a user on a second lateral side of the user opposite the first lateral side, and a second component having a first end securing to the first component and said second component arranged to extend across an anterior side of the user such that a second end of the second component connects to the sling; a second strap system having a first strap arranged to extend about a first or ipsilateral shoulder on the first lateral side of the user, and a second strap extending from the first strap on a posterior side of the user and extending to the waist stabilizer, wherein the second strap system includes a junction arranged on the posterior side of the user to adjust a first end of the second strap relative to the first strap of the second strap system;
 a waist stabilizer arranged to encircle the user's waist and connect to the second end of the second component.

2. The shoulder harness of claim 1, wherein a junction of the first and second components forms a Y-shape.

3. The shoulder harness of claim 1, further comprising a lateral support connecting the waist stabilizer to the second end of the second component, the lateral support adapted to connect to the sling.

4. The shoulder harness of claim 3, wherein the lateral support is a rigid or semi-rigid plate.

5. The shoulder harness of claim 3, wherein a second end of the first strap system is adjustably secured to the lateral support.

6. The shoulder harness of claim 1, wherein the first component of the first strap system fully encircles the second or contralateral shoulder.

7. The shoulder harness of claim 1, wherein a second end of the second strap of the second strap system is arranged to adjustably secure to the waist stabilizer.

8. The shoulder harness of claim 7, wherein the second end of the second strap of the second strap system is arranged to secure over the anterior side of the user.

9. The shoulder harness of claim 1, wherein the first component is adapted to provide stabilization to the sling by extending about the second or contralateral shoulder to the first lateral side of the user and arranged to extend a distance from the user's neck to concentrate suspension of the sling about the second or contralateral shoulder.

10. An orthopedic device having anterior and posterior sides, and adapted for securing over first and second opposed shoulders on first and second lateral sides of a user, respectively, the orthopedic device comprising:
 a waist stabilizer adapted to secure about a waist of the user; and
 a first strap system configured to extend about the first lateral side of the user and having first and second components, the first component arranged generally as circular in shape to extend about one of the first and second opposed shoulders, the second component having a first end secured to the first component and arranged to extend obliquely about the user's anterior chest such that a second end of the second component secures to the waist stabilizer; a second strap system having a first strap arranged to extend about a first opposed shoulder on the first lateral side of the user, and a second strap extending from the first strap on a posterior side of the user and extending to the waist stabilizer;
 a splint connected to the waist stabilizer and the second end of the second component of the first strap system.

11. The orthopedic device of claim 10, wherein the splint is arranged to adjustably connect to the second lateral side of the user.

12. The orthopedic device of claim 10, further comprising a lateral support connecting the waist stabilizer to the second end of the second component.

13. The orthopedic device of claim 12, wherein the second end of the second component is adjustably secured to the lateral support.

14. The orthopedic device of claim 12, wherein the splint is adjustably secured to the lateral support.

15. The orthopedic device of claim 10, wherein the second strap system includes a junction arranged onto the posterior side of the user to adjust a first end of the second strap relative to the first strap of the second strap system.

16. The orthopedic device of claim 10, wherein a second end of the second strap of the second strap system is arranged to adjustably secure to the waist stabilizer.

17. The orthopedic device of claim 16, wherein the second end of the second strap of the second strap system is arranged to secure over an anterior side of the user.

* * * * *